US011141676B2

(12) United States Patent
Lee

(10) Patent No.: US 11,141,676 B2
(45) Date of Patent: Oct. 12, 2021

(54) SYSTEM FOR ENERGY REGENERATION USING MECHANICAL VAPOR RECOMPRESSION IN COMBINED CHEMICAL PROCESS

(71) Applicant: SUNTECO LIMITED, Gyeonggi-do (KR)

(72) Inventor: Joo Sun Lee, Gyeonggi-do (KR)

(73) Assignee: SUNTECO LIMITED, Gyeonggi-do (KR)

( * ) Notice: Subject to any disclaimer, the term of this patent is extended or adjusted under 35 U.S.C. 154(b) by 30 days.

(21) Appl. No.: 16/651,757

(22) PCT Filed: Jul. 12, 2018

(86) PCT No.: PCT/KR2018/007904
§ 371 (c)(1),
(2) Date: May 15, 2020

(87) PCT Pub. No.: WO2019/066220
PCT Pub. Date: Apr. 4, 2019

(65) Prior Publication Data
US 2020/0282327 A1    Sep. 10, 2020

(30) Foreign Application Priority Data

Sep. 29, 2017  (KR) .................. 10-2017-0127142

(51) Int. Cl.
*B01D 1/00*    (2006.01)
*B01D 1/30*    (2006.01)
(Continued)

(52) U.S. Cl.
CPC ............ *B01D 1/0058* (2013.01); *B01D 1/30* (2013.01); *B01D 3/32* (2013.01); *B01J 8/008* (2013.01);
(Continued)

(58) Field of Classification Search
None
See application file for complete search history.

(56) References Cited

U.S. PATENT DOCUMENTS 5,763,691 A  *  6/1998  Kawabe .................. C07C 29/12
568/858

FOREIGN PATENT DOCUMENTS

KR    1019870000542 A    2/1988
KR    10-0450234 B1    9/2004
(Continued)

OTHER PUBLICATIONS

International Search Report for PCT/KR2018/007904, dated Nov. 14, 2018, 4 pages.

*Primary Examiner* — Derek N Mueller
(74) *Attorney, Agent, or Firm* — Saliwanchik, Lloyd & Eisenschenk

(57) ABSTRACT

The present disclosure provides a system for energy recycling using mechanical vapor recompression in combined chemical process, the system including a heat exchange reactor for generating an intermediate material by means of an exothermic reaction and discharging the generated intermediate material, and heat-exchanging heat generated in the exothermic reaction with water supplied from outside so as to generate water vapor; an absorption tank for receiving the intermediate material, and mixing the intermediate material with water, so as to generate an intermediate material aqueous solution; a stripper for receiving the intermediate material aqueous solution, and separating the intermediate material into an intermediate material gas and an intermediate material water-rich aqueous solution; an endothermic reactor for receiving the intermediate material water-rich aqueous solution, and reacting the intermediate material with water, so as to generate a final product aqueous solution; an evaporation concentrator for receiving the final (Continued)

product aqueous solution, and heat-exchanging heat of the water vapor from the heat exchange reactor with the final product aqueous solution so as to generate steam; a dehydrating distillation tower for receiving, dehydrating, and purifying the final product aqueous solution discharged from the evaporation concentrator; and a mechanical vapor recompressor for compressing the steam from the evaporation concentrator, and providing the compressed steam as a source of heat or a source of steam supply.

20 Claims, 4 Drawing Sheets

(51) Int. Cl.
    *B01D 3/32*     (2006.01)
    *B01J 8/00*     (2006.01)

(52) U.S. Cl.
    CPC .................. *B01J 2208/0007* (2013.01); *B01J 2208/00053* (2013.01); *B01J 2208/00362* (2013.01)

(56) References Cited

FOREIGN PATENT DOCUMENTS

| | | | |
|---|---|---|---|
| KR | 1020150118446 A | 12/2015 | |
| KR | 1020160116358 A | 11/2016 | |
| KR | 1020170011886 A | 3/2017 | |
| KR | 10-1811561 B1 | 12/2017 | |

* cited by examiner

SYSTEM FOR ENERGY REGENERATION USING MECHANICAL VAPOR RECOMPRESSION IN COMBINED CHEMICAL PROCESS

CROSS REFERENCE TO RELATED APPLICATION

The present application is the national stage entry of International Patent Application No. PCT/KR2018/007904, having a filing date of Jul. 12, 2018, which claims priority to and the benefit of Korean Patent Application No. 10-2017-0127142 filed in the Korean Intellectual Property Office on Sep. 29, 2017, the entire contents of which are incorporated herein by reference.

1. FIELD

The present disclosure relates to a system for recycling the steam generated in a chemical reaction process for producing a polymer chemical product, and more particularly, to a system for efficiently applying the steam generated in the process where an exothermic process and an endothermic process of the chemical reaction are combined, and the necessary heat, in accordance with respective process characteristics, so as to redistribute and self-supply the energy necessary in an entirety of the system.

2. BACKGROUND

Chemical reaction processes for producing polymer chemical products are widely used, and polymer chemical products are typically manufactured using hydrocarbons.

These hydrocarbons are being produced through various chemical reaction processes, as chemical products, pharmaceutical products, and various polymer chemical products necessary for daily life. Especially, typical polymer chemical products manufactured using hydrocarbons include ethylene oxide, methylene oxide, propylene oxide, butylene oxide, ethylene glycol, methylene glycol, propylene glycol, and butylene glycol.

Ethylene oxide has a very high chemical reactivity, and thus reacts well with water, alcohol, acid, and amines to produce numerous derivatives. Ethylene oxide is also inexpensive, and thus widely used as a synthetic raw material in numerous fields. In particular, ethylene oxide is most frequently used to produce ethylene glycol. Ethylene glycol is the greatest derivative of ethylene oxide, and is used as an antifreeze for automobiles, etc., and is widely used as a raw material for polyester fibers.

A petrochemical process for decomposition and combination of such hydrocarbons uses a large amount of thermal energy, but little is known about any active measures to save such energy.

In addition, the process of producing polymer chemical products using hydrocarbons as raw material consists of various processes such as an exothermic reaction process, an endothermic reaction process, and a process using thermal energy, etc. The water vapor produced in the exothermic reaction process is partially used in the subsequent processes, but the thermal energy needed in most processes is covered by the thermal energy supplied from an additional external heat source. Not only that, the externally supplied steam is used for most of the water vapor required during operation of the system.

In a system used in the petrochemical process, demand for thermal energy is very high overall, and depending on the process, a large amount of steam is required, and to supply both such thermal energy and water vapor from outside, the cost of installing and operating the corresponding supply device is considerable.

SUMMARY

The present disclosure is introduced to solve the above-mentioned problems.

A purpose of the present disclosure is to, instead of seeking the required thermal energy from an additional external heat source, but to go beyond the passive method of adjusting the number of stages in an evaporation concentrator and actively introduce an MVR system for compressing the steam generated in a evaporation concentrator and add the thermal energy generated from the MVR to the remaining processes, so that the steam generated in a chemical process system, in particular the steam generated in an oxidation exothermic reaction, can be completely consumed in a subsequent dehydration process caused by evaporation concentration, thereby reducing the cost and effort necessary for supplying additional thermal energy.

Further, another purpose of the present disclosure is to, instead of receiving even the steam required inside the chemical process system from outside, but to directly compress and recycle the steam generated at a rear stage of the process of the chemical process system, thereby reducing the cost and effort necessary for supplying additional steam.

In order to achieve the aforementioned purposes, the present disclosure provides a system for energy recycling using mechanical vapor recompression in combined chemical process, including a heat exchange reactor for generating an intermediate material by means of an exothermic reaction and discharging the generated intermediate material, and heat-exchanging heat generated in the exothermic reaction with water supplied from outside so as to generate water vapor; an absorption tank for receiving the intermediate material, and mixing the intermediate material with water, so as to generate an intermediate material aqueous solution; a stripper for receiving the intermediate material aqueous solution, and separating the intermediate material into an intermediate material gas and an intermediate material water-rich aqueous solution; an endothermic reactor for receiving the intermediate material water-rich aqueous solution, and reacting the intermediate material with water, so as to produce a final product aqueous solution; an evaporation concentrator for receiving the final product aqueous solution, and heat-exchanging heat of the water vapor from the heat exchange reactor with the final product aqueous solution so as to generate steam; a dehydrating distillation tower for receiving, dehydrating, and purifying the final product aqueous solution discharged from the evaporation concentrator; and a mechanical vapor recompressor for compressing the steam from the evaporation concentrator, and providing the compressed steam as a source of heat or a source of steam supply.

Preferably, the evaporation concentrator may be composed of a multi-stage evaporation concentrator in which a plurality of evaporation concentrators are sequentially connected, and the number of stages of the multi-stage evaporation concentrator may be determined according to the temperature and pressure of the steam required in the mechanical vapor recompressor, in consideration of the concentration of the final product aqueous solution discharged from the evaporation concentrator and the amount of discharge heat of the water vapor generated in the heat exchange reactor.

Preferably, the evaporation concentrator forming the multi-stage evaporation concentrator may be a natural circulation type evaporation concentrator.

Preferably, the evaporation concentrator forming the multi-stage evaporation concentrator may be a falling film evaporator.

Preferably, the mechanical vapor recompressor may be in fluid communication with the endothermic reactor, such that the endothermic reactor receives heat from the steam discharged from the mechanical vapor recompressor.

Preferably, a reboiler of the dehydrating distillation tower may be in fluid communication with the mechanical vapor recompressor, such that the dehydrating distillation tower receives heat from the steam.

Preferably, a reboiler of the stripper may be in fluid communication with the mechanical vapor recompressor, such that the stripper receives heat from the steam.

Preferably, the system may further include a distillation tower provided to condense the intermediate material gas discharged from the stripper so as to receive the intermediate material as an intermediate material solution, and, in an upper portion of the distillation tower, to distill the intermediate material so as to discharge the intermediate material as a pure intermediate material, and, in a lower portion of the distillation tower, to discharge the remaining intermediate material solution so as to supply the remaining intermediate material solution to the endothermic reactor.

Preferably, a reboiler of the distillation tower may be in fluid communication with the mechanical vapor recompressor, such that the distillation tower receives heat from the steam.

Preferably, the steam of the mechanical vapor recompressor may be in fluid communication with a cooling water preheater of the heat exchange reactor so as to preheat cooling water supplied to the heat exchange reactor.

Preferably, a mechanical vapor recompressor may be additionally disposed between the mechanical vapor recompressor and the stripper, or between the mechanical vapor recompressor and the cooling water preheater of the heat exchange reactor.

Preferably, the intermediate material may be ethylene oxide, and the final product may be ethylene glycol.

According to the present disclosure, instead of using an external heat source for the thermal energy and steam necessary in the chemical process system, by adopting an appropriate design of an MVR system so as to directly produce and self-supply the steam necessary in each process at an appropriate pressure and flow rate, it is possible to greatly reduce the cost and effort required in supplying the thermal energy and steam.

Further, by using a falling film evaporator as the evaporation concentrator in the chemical process system of the present disclosure where the MVR is applied, compared to when a natural circulation type evaporation concentrator is used, the temperature conditions of a primary steam can be designed more flexibly, and the temperature of a secondary steam can be further increased, and the amount of use of pure steam can be reduced.

DETAILED DESCRIPTION

Hereinafter, the energy recycling system in a chemical process according to the present disclosure will be described in detail with reference to the accompanying drawings.

Figure 1:
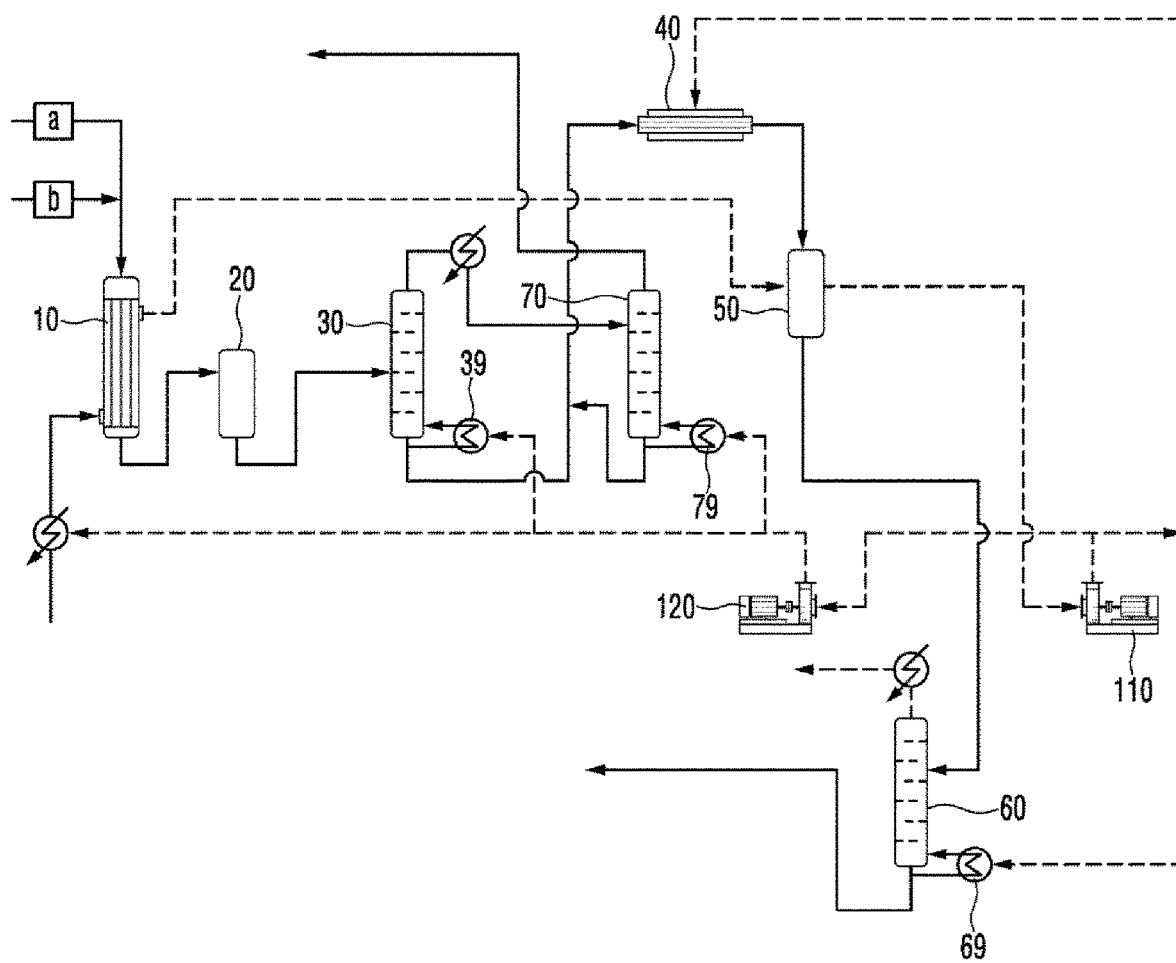
FIG. 1 is a view schematically illustrating a system according to the present disclosure.
Figure 2:
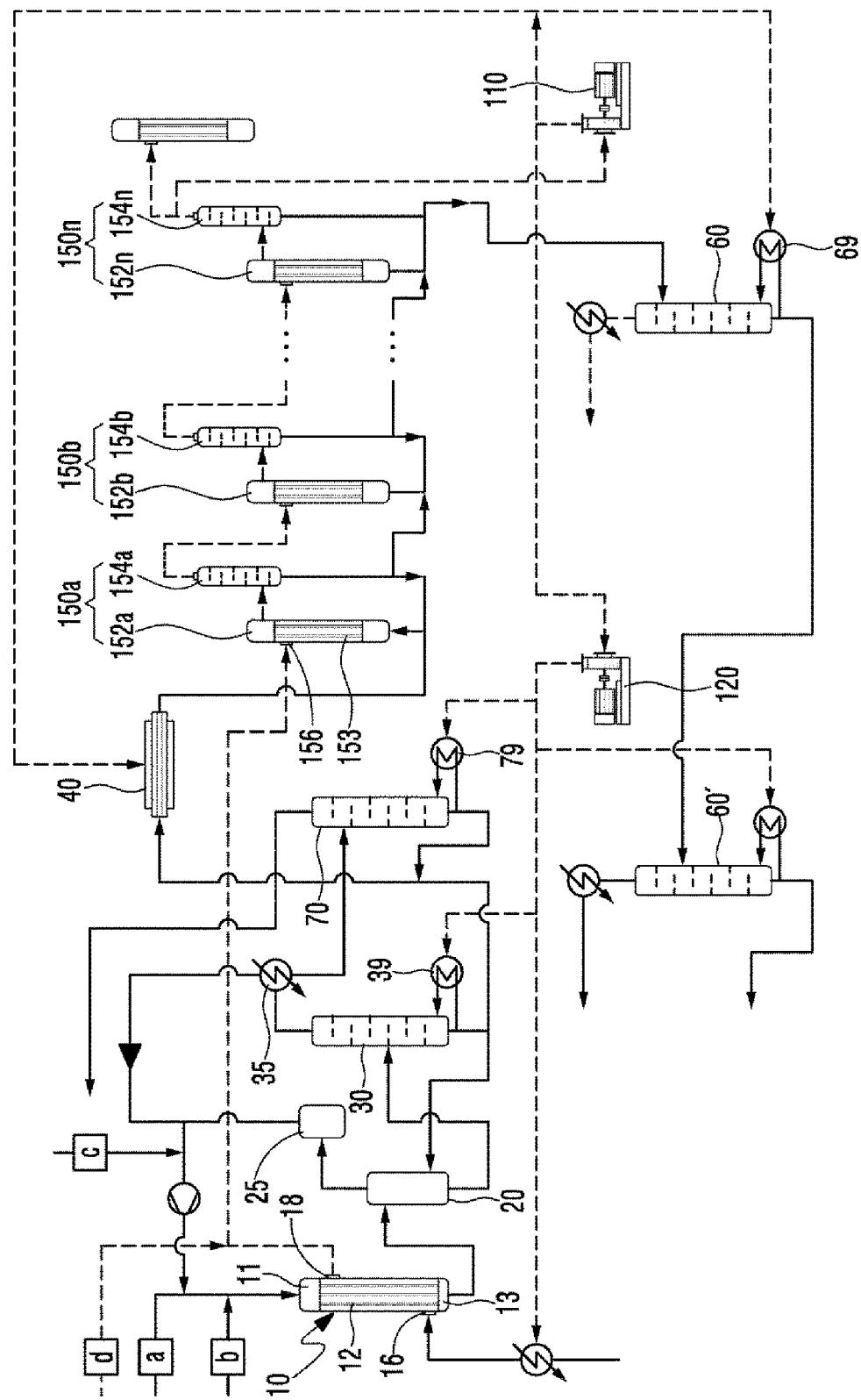
FIG. 2 is a view illustrating an embodiment of the system according to the present disclosure.

FIG. 1 is a view schematically illustrating the system according to the present disclosure, and FIG. 2 is a view illustrating an embodiment where the system according to the present disclosure, is specified.

As can be seen in FIG. 1, main raw materials a, b are put into a heat exchange reactor 10 together with an auxiliary gas.

The heat exchange reactor 10 is a multi-tube type reactor, in which tubes through which a reactant passes are installed inside a housing and water flows into the housing to exchange heat by contacting the outside of the tube.

With the main raw material and auxiliary gas flown into the heat exchange reactor 10, when a predetermined catalyst is used to cause a reaction, an oxidation reaction occurs accompanied by a significant heat generation.

Water is flown from outside into the heat exchange reactor 10, and as the water receives heat generated by the exothermic reaction inside the heat exchange reactor 10, the water is evaporated and discharged as water vapor. This water vapor is to be called a primary steam.

The reaction in the heat exchange reactor 10 generates an intermediate material solution in which the gas is mixed. Then, the intermediate material solution is gathered in a lower portion of the heat exchange reactor, and is discharged.

The intermediate material discharged from the heat exchange reactor 10 flows into an absorption tank 20, washed with water, and then discharged as the intermediate material aqueous solution.

The intermediate material aqueous solution discharged from the absorption tank 20 flows into a stripper 30. In the stripper 30, the intermediate material aqueous solution is separated into water, impurities and gas. The intermediate material gas is discharged from an upper portion of the stripper 30, and if this intermediate material gas is condensed and sent to a distillation tower 70 and then is purified in the distillation tower, a pure intermediate material such as ethylene oxide, that will be described below, can be obtained and used as a final product. At the same time, from a lower portion of the stripper 30, an intermediate material water-rich aqueous solution is discharged.

The intermediate material water-rich aqueous solution discharged from the stripper 30 flows into an endothermic reactor 40. The endothermic reactor 40 is a multi-tube reactor, in which tubes through which the intermediate material water-rich aqueous solution passes are installed inside a housing, and steam flowing into the reactor from outside contacts the outside of the tubes of the endothermic reactor in order to transfer heat to the tube.

In the endothermic reactor 40, the intermediate material water-rich aqueous solution and water react to generate a final product aqueous solution. The reaction from which the final product aqueous solution is generated, is an endothermic reaction, and the heat to be used in the endothermic reaction is received from the steam.

The final product aqueous solution discharged from the endothermic reactor 40 enters an evaporation concentrator 50 in a state of a low concentration.

The evaporation concentrator 50 is a multi-tube type reactor, in which tubes through which the final product aqueous solution passes are installed inside a housing, and water vapor flowing into the housing (that is, the primary steam) exchanges heat by contacting the outside of the tube.

The evaporation concentrator 50 receives the primary steam, that is, the water vapor generated in the heat exchange reactor, and uses heat of the primary steam to evaporate the final product aqueous solution, thereby concentrating the final product aqueous solution. The steam evaporated from the final product aqueous solution will be called a secondary steam.

From a lower portion of the evaporation concentrator 50, the final product aqueous solution which is concentrated as moisture is reduced by the evaporation, is discharged and sent to a dehydrating distillation tower 60.

In the dehydrating distillation tower 60, the final product aqueous solution is heated, thereby in a lower portion of the tower, removing most of the moisture from the final product aqueous solution, and in an upper portion of the tower, discharging water vapor having a low pressure, and thereafter the water vapor is condensed.

Further, when necessary, one or more distillation tower 60 may be added and provided as a multi-stage distillation tower. When using the multi-stage distillation tower, if the final product aqueous solution is an ethylene glycol aqueous solution as will be described below, it can be separated into mono ethylene glycol (MEG), di-ethylene glycol (DEG), and tri-ethylene glycol (TEG) to obtain high purity products, respectively.

According to the present disclosure, the low-pressure secondary steam generated in the evaporation concentrator 50, is compressed in a mechanical vapor recompressor 110, and distributed to surrounding processes requiring thermal energy. The mechanical vapor recompressor may compress the secondary steam to suit the pressure of the steam required in the surrounding processes, and supply the steam to a device that needs the steam.

The mechanical vapor recompression (MVR) system is a mechanical evaporation recompressor device that compresses low pressure steam to generate high pressure steam. In the industrial fields, various types of mechanical vapor recompressors are used, including centrifugal compressors that compress the gas by converting velocity energy into pressure energy by means of the centrifugal force of a high-speed rotating impeller.

According to the present disclosure, examples for utilizing the secondary steam compressed in the mechanical vapor compressor are as follows.

Figure 4:
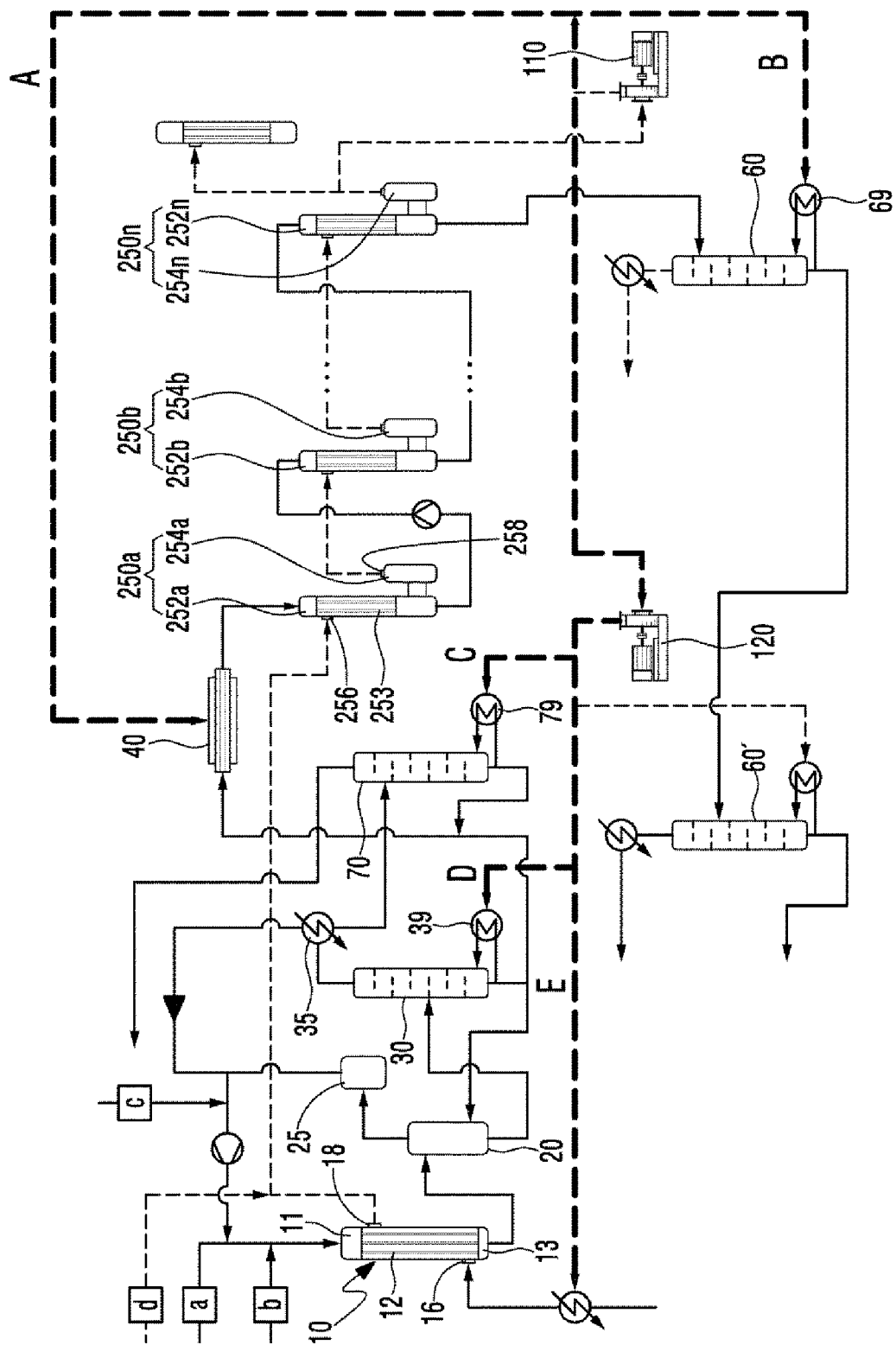
FIG. 4 is a view describing an example where steam is utilized in the system of FIG. 3.

First, it may supply the heat to be used in an endothermic reaction of the endothermic reactor 40 (refer to A in FIG. 4).

Secondly, the steam may be supplied to a reboiler 39, 69, 79 installed in the distillation tower or the stripper, so as to be used as a heat source for the reboiler of the distillation tower or the stripper (refer to B, C and D of FIG. 4). In this case, when necessary, another mechanical vapor recompressor 120 may be disposed to additionally compress the steam.

Thirdly, it may be used to preheat the cooling water supplied to the heat exchange reactor 10 (refer to E of FIG. 4).

As described above, the present disclosure presents a new way of not discarding the energy generated at a rear stage of the process, but using the energy generated by applying the mechanical vapor recompressor, in required processes, and thereby substantially achieving a self-supplying energy balance.

That is, instead of discarding the steam discharged from the evaporation concentrator 50, but by using the mechanical vapor recompressor in recycling the steam, it is possible to greatly reduce the thermal energy and cost it takes to operate the system, and thereby improve economic feasibility.

Not only that, since it is unnecessary to supply additional steam from outside during operation of the system, there is no need for additional device to supply steam either, and thus installation cost and operation cost of the corresponding device can be excluded, and thereby improve economic feasibility.

Hereinafter, the present disclosure will be described based on specific embodiments with reference to FIGS. 2 to 4. For reference, the components described below are in fluid communication with each other so that fluids can move along a path indicated by solid lines and dotted lines.

Figure 3:
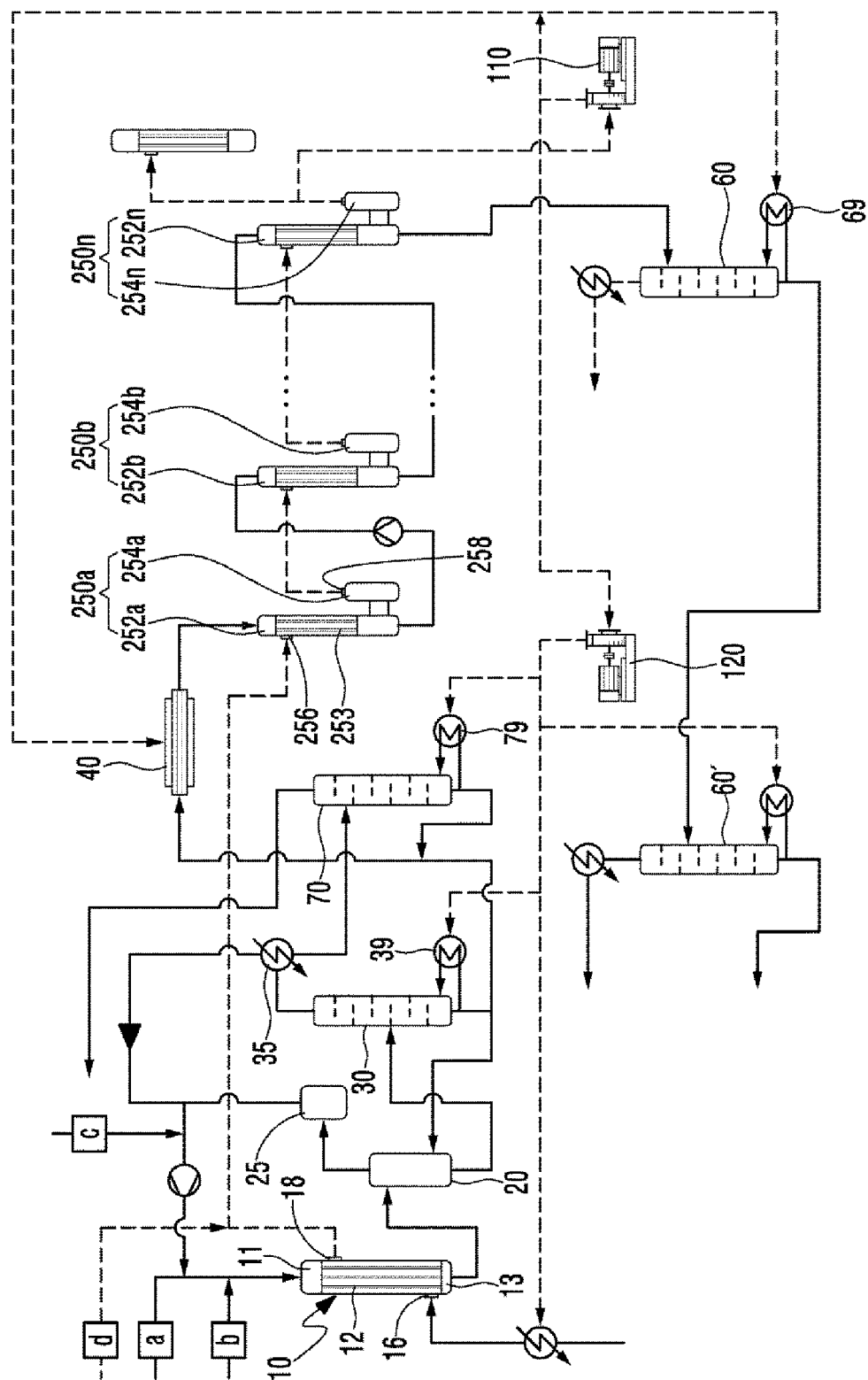
FIG. 3 is a view illustrating another embodiment of the system according to the present disclosure.

In FIGS. 2 to 4, the solid lines indicate the path along which the reactant, intermediate material and final product may pass, and the dotted lines indicate the path along which the steam may pass. Especially in FIG. 4, bold dotted lines and symbols (A to E) are used to clearly reveal an example where the secondary steam is utilized.

In a complex chemical process, various materials can be selected as the main raw material as needed, to produce the desired intermediate material and final product. Hereinafter, the process of generating ethylene oxide (EO) and ethylene glycol (EG) by using ethylene and oxygen as the main raw materials, will be described as an example.

In the heat exchange reactor 10, low molecular hydrocarbon ethylene (a) ($H_2C_4$) and oxygen (b) ($O_2$) are supplied as raw materials. Further, an auxiliary gas (c), such as methane and nitrogen, may be additionally injected into the heat exchange reactor 10, and a reaction may be performed using a catalyst in which silver is finely dispersed. Then, in the heat exchange reactor 10, an oxidation reaction accompanied by a heat generation, occurs, and ethylene oxide (EO) is generated as an intermediate material.

The heat exchange reactor 10 is a multi-tube reactor, in which tubes 12 through which reactants may pass, are disposed. Further, the heat exchange reactor 10 includes a housing, that is, a shell portion surrounding the tube 12, and also includes an inlet 16 into which cooling water flows, and an outlet 18 through which vapor is discharged. This water vapor will be called the primary steam.

Since the pressure and flow rate of the primary steam affect the yield of the oxidation exothermic reaction, the pressure and flow rate of the primary steam are controlled to suit the maximum yield. Further, the pressure and flow rate of the primary steam become the criteria for determining the number of stages of a multi-stage evaporation concentrator 50 at the rear stage.

The cooling water flown in through the inlet 16 contacts the tube 12 disposed inside the heat exchange reactor, and receives the heat from the reactant passing through the inside of the tube, and then discharged through the outlet 18 as water vapor.

At the same time, after transferring heat to the cooling water, the reactant flows into the absorption tank 20 as an ethylene oxide solution mixed with gas.

In the absorption tank 20 that is in fluid communication with the heat exchange reactor 10, the ethylene oxide is washed with water, to be supplied to the stripper 30 as the ethylene oxide aqueous solution. The gas separated in the absorption tank 20 may pass through a separation tank 25 (gas scrubber; wash tank), and may be supplied back to the heat exchange reactor 10.

In the stripper 30 that is in fluid communication with the absorption tank 20, the ethylene oxide aqueous solution is separated into water, impurities and gas, and from the upper portion of the stripper 30, the gas is discharged, and from the lower portion of the stripper 30, ethylene oxide water-rich aqueous solution is discharged.

The ethylene oxide gas discharged from the upper portion of the stripper 30, is condensed through a condenser 35, and then flows into the distillation tower 70. In the distillation tower 70, the ethylene oxide solution is purified, to be discharged as pure ethylene oxide. The ethylene oxide prepared as such may be used as a final product.

The stripper 30 is in fluid communication with the endothermic reactor 40 so that the ethylene oxide water-rich aqueous solution discharged from the lower portion of the stripper 30 is supplied to the endothermic reactor 40.

In the endothermic reactor 40, ethylene glycol is generated as a final product by means of an endothermic reaction. Especially, in the endothermic reaction reactor, by means of a reaction with an excess amount of water (approximately 5 to 10 times), an ethylene glycol aqueous solution is obtained.

As the ethylene glycol aqueous solution generated in the endothermic reactor 40 is concentrated, dehydrated and purified in the process that will be described below, a final ethylene glycol may be prepared.

The endothermic reactor 40 is in fluid communication with the evaporation concentrator 50, and thus the ethylene glycol aqueous solution generated in the endothermic reactor 40 flows into the evaporation concentrator 50.

The evaporation concentrator 50 is a multi-tube type reactor, in which tubes are provided to pass an aqueous solution of the final product, that is, the ethylene glycol aqueous solution, through the tubes. Further, the evaporation concentrator 50 includes a shell corresponding to a housing surrounding the tube, the shell having a water vapor inlet through which water vapor may flow into the shell.

At an initial stage of operation, a pure steam (d) may be supplied to the evaporation concentrator 50. During a normal operation, the water vapor (primary steam) generated in the heat exchange reactor 10 flows in through the water vapor inlet, transfers heat to the ethylene glycol aqueous solution inside the tube, and thereby evaporates the ethylene glycol aqueous solution to generate vapor. This vapor is called the secondary steam, and this secondary steam is discharged through a steam outlet as a low pressure steam.

Meanwhile, the evaporation concentrator 50 may be formed to have multiple stages in order to increase the concentration of the ethylene glycol. That is, as can be seen from FIGS. 2 to 4, the evaporation concentrator 50 may be formed to have multiple stages (for example, 2 to 7 stages) by sequentially connecting a plurality of evaporation concentrators. Thus, the concentration of the ethylene glycol can be increased through numerous evaporation processes.

That is, in the multi-stage evaporation concentrator, when the primary steam, which is the water vapor generated in the heat exchange reactor 10, flows into a first stage evaporation concentrator, in the first stage evaporation concentrator 150a, 250a, the primary steam heats the final product aqueous solution, and the steam evaporated from the final product aqueous solution flows into a second stage evaporation concentrator 150b, 250b. Further, the final product aqueous solution, concentrated as a result of being heated at the first stage evaporation concentrator to reduce moisture, flows into the second stage evaporation concentrator. This process is proceeded sequentially through numerous stages of evaporation concentrator, thereby further gradually concentrating the final product aqueous solution. Here, based on the pressure and flow rate of the primary steam, the number of stages of the evaporation concentrator is determined, and when determining the number of stages of the evaporation concentrator, the amount of heat of each stage and the temperature difference between respective stages necessary for 1/n of the total evaporation amount are considered as well.

Meanwhile, when the evaporation concentrator is formed as an evaporation concentrator of a high number of stages, it is possible to increase the concentration of the ethylene glycol and reduce the dehydration load of the subsequent dehydrating distillation tower 60. However, when the number of stages is increased, relatively the temperature of the secondary steam lowers, and thus in the present disclosure which intends to compress the secondary steam in the mechanical vapor recompressor 110 to supply the amount of heat required in the remaining processes, the temperature of the secondary steam becoming too low is not desirable.

Therefore, in the present disclosure utilizing the mechanical vapor recompressor 110, the temperature of the secondary steam flowing into the mechanical vapor recompressor 110 should be appropriately adjusted in consideration of energy efficiency. That is, in the present disclosure, in order to optimize the efficiency of steam recycling in the complex chemical process, it is desirable to adjust the number of stages of the evaporation concentrator 50 in consideration of the discharge concentration of the final product, that is, ethylene glycol, and the discharge heat amount of the heat exchange reactor 10.

FIG. 2 illustrates an embodiment where each of the evaporation concentrators used in the multi-stage evaporation concentrator, is a natural circulation type evaporation concentrator, that is, a thermo-syphon evaporator.

In industrial sites performing complex chemical processes, natural circulation type evaporation concentrators are generally used as evaporation concentrators. The natural circulation type evaporation concentrator is a well-known configuration in the related art, and thus detailed description will be omitted. Using the natural circulation type evaporation concentrator has an advantage of operating without pumps by using the head drop having circulation power.

Each of the natural circulation type evaporation concentrator 150a, 150b, . . . , 150n consists of an evaporator 152a, 152b, . . . , 152n, and a chamber 154a, 154b, . . . , 154n. To simply describe the configuration of the natural circulation type evaporation concentrator, after flowing into a lower portion of the evaporator 152a of the first stage natural circulation type evaporation concentrator 150a, the final product aqueous solution is heated, and thereby rises to an upper portion of the evaporator 152a through the tube 153a. The heating of the final product aqueous solution is achieved by the primary steam generated in the heat exchange reactor 10 and flowing into the evaporator 152a through the inlet 156. At the initial stage of operation, pure steam (d) may be supplied.

The heated final product aqueous solution goes into the chamber 154a, steam is discharged through an upper portion of the chamber 154a, and the concentrated remaining final product aqueous solution is discharged at a lower portion of the chamber 154a and then is circulated again or transferred to a next stage evaporator. The discharged steam and the final product aqueous solution flow into the next stage evaporator, that is, the evaporator 152b of the second stage evaporation concentrator 150b, to repeat the aforementioned evaporation concentration process. This process is performed sequentially until the final stage.

In the present disclosure using the mechanical vapor recompressor 110, if the temperature of the secondary steam flowing into the mechanical vapor recompressor 110 is too low, there might be a problem where, even when the secondary steam is compressed, the risen temperature cannot reach the required temperature, and thus the compressed secondary steam cannot be used, or a multi-stage mechanical vapor recompressor must be used in order to compress the steam to the required temperature. Therefore, the system must be designed such that the temperature of the steam flowing into the mechanical vapor recompressor 110, that is, the secondary steam, reaches an adequate temperature, as described above.

Specifically, in relation to the design of the system, the following must be considered. In the natural circulation type evaporation concentrator, the final product aqueous solution flows into a lower side of the tube 153 of the evaporator 152 and rises to an upper portion of the evaporator 152, and thus in order to heat and evaporate the final product aqueous solution at the lower side of the tube 153, the difference of saturation temperature based on the difference of pressure between the lower portion and the upper portion must be considered as well. That is, in order to evaporate the final product aqueous solution, in designing the system, considering the difference of saturation temperature between the lower portion and the upper portion of the tube, the temperature of the primary steam being supplied to the evaporation concentrator should be increased. Further, since it is a multi-stage evaporation concentrator, the temperature of the primary steam should be increased by the difference of saturation temperature multiplied by the corresponding number of stages.

Next, FIG. 3 illustrates an embodiment where each of the evaporation concentrator used in the multi-stage evaporation concentrator is a falling film evaporator.

Each of the falling film evaporator 250a, 250b, . . . , 250n is a multi-tube reactor, which includes an evaporator 252a, 252b, . . . , 252n, and a chamber 254a, 254b, . . . , 254n connected to the evaporator. Inside the evaporator, there is a tube 253 provided for the final product aqueous solution, which is ethylene glycol aqueous solution, to pass through. Further, the evaporation concentrator includes a housing that surrounds the tube, that is, a shell, and also a water vapor inlet 256 installed in the evaporator, and a steam outlet 258 installed in the chamber 254.

At an initial stage of operation, additional pure steam (d) may be supplied to the evaporation concentrator 250, and during normal operation, the vapor generated in the heat exchange reactor 10 (primary steam) flows in through the water vapor inlet 256.

The final product aqueous solution is supplied to an upper portion of the first stage evaporation concentrator 250a, and as it flows downwards through the tube 253 of the evaporator 252a, it is heated by the primary steam. As the heated final product aqueous solution is evaporated, it moves to a gas-liquid separator in a lower portion of the evaporator 252a. The final product aqueous solution heated by the primary steam is evaporated, and discharged via the chamber 254a as steam, and the steam generated from the final product is called the secondary steam. Further, the final product aqueous solution concentrated as moisture is reduced by means of evaporation, is discharged at the lower portion of the evaporator 252a.

The steam and the final product aqueous solution discharged from the first stage evaporation concentrator 250a, flow into the next stage evaporation concentrator, that is, the second stage evaporation concentrator 250b, by means of a pump. Here, the steam discharged from the first stage evaporation concentrator is used to evaporate the final product aqueous solution flowing into the next stage.

The ethylene glycol aqueous solution having a reduced amount of moisture due to evaporation, is discharged from the lower portion of the final stage evaporation concentrator, and then supplied to the dehydrating distillation tower 60 that is in fluid communication with the evaporation concentrator.

Meanwhile, the use of the falling film evaporator for each evaporation concentrator of the multi-stage evaporation concentrator has a few advantages as described below, in comparison to when the natural circulation type evaporation concentrator is used.

First, the falling film evaporator has advantages over the natural circulation type evaporation concentrator when designing the system. In the falling film evaporator, the final product aqueous solution is supplied to the upper portion of the evaporator, and thus there is no need to consider the difference of saturation temperature between the upper portion and the lower portion of the evaporator in determining the temperature of the primary steam. Therefore, when using the evaporation concentrator having the same number of stages, in the case of using the falling film evaporator, the temperature of the primary steam may be designed to be lower than when using the natural circulation type evaporation concentrator.

Secondly, based on the aforementioned principle, when the primary steam of a same temperature is supplied while using the evaporation concentrator having the same number of stages, the temperature of the secondary steam obtained in the falling film evaporator is higher than the temperature of the secondary steam obtained in the natural circulation type evaporator. Therefore, the temperature of the secondary steam flowing into the mechanical vapor recompressor can be increased, making it possible to further utilize the secondary steam, and reduce the number of the mechanical vapor recompressors.

Thirdly, when using the natural circulation type evaporation concentrator, it takes more time to normalize the operation, and a large amount of pure steam must be supplied at the initial stage of operation. On the other hand, when using the falling film evaporator, it takes relatively less time to normalize the operation, and thus less amount of pure steam can be used at the initial stage of operation.

Next, to describe the dehydrating distillation tower 60 into which the final product aqueous solution flows, the dehydrating distillation tower 60 is a device for finally removing the moisture from the ethylene glycol aqueous solution. Through the dehydrating distillation tower 60, a dehydrated final ethylene glycol product can be obtained.

Preferably, when necessary, it is possible to configure a multi-stage dehydrating distillation tower by additionally disposing a dehydrating distillation tower 60. Normally, when preparing ethylene glycol, di-ethylene glycol is produced at approximately 9 to 10%, and tri-ethylene glycol is produced at approximately 2 to 3% as well. In this situation, by using the multi-stage dehydrating distillation tower 60, 60', by means of the distillation method, the ethylene glycol may be separated and obtained as mono ethylene glycol (MEG), di-ethylene glycol (DEG), and tri-ethylene glycol (TEG).

The secondary steam discharged from the evaporation concentrator 50 is supplied to the mechanical vapor recompressor MVR 110 instead of being discarded. The secondary steam may be compressed in the mechanical vapor recompressor 110, and appropriately supplied to the required processes in the system.

The process of generating the ethylene glycol through the endothermic reactor 40 is an endothermic reaction, and in order to supply the steam to be used in the endothermic reaction, an additional steam generation device is needed, and therefore, it takes considerable cost to install and operate the steam generation device. However, as indicated by A in FIG. 4 of the present disclosure, by recompressing the secondary steam discharged from the evaporation concentrator 50 and supplying the recompressed steam to the endothermic reactor 40, to recycle the secondary steam, it is possible to eliminate the cost associated with the additional steam generation device, and thereby greatly increase the economic feasibility.

Further, the secondary steam compressed in the mechanical vapor recompressor 110 may be added to the pure steam to be used in the present system, and play a role of supplementing the pure steam.

Further, the secondary steam compressed in the mechanical vapor recompressor 110 may be used as a heat source required in each device of the system. Specifically, the secondary steam may be supplied to the reboiler 69 used in the dehydrating distillation tower 60, as indicated by B in FIG. 4, supplied to the reboiler 79 used in the distillation tower 70 as indicated by C in FIG. 4, supplied to the reboiler 39 used in the stripper 30 as indicated by D in FIG. 4, and supplied to the cooling water preheater of the heat exchange reactor 10 to preheat the cooling water flowing into the heat exchange reactor 10 as indicated by E in FIG. 4.

Preferably, the secondary steam discharged from the mechanical vapor recompressor 110 may be additionally compressed through additional mechanical vapor compressors 120, 130 when deemed necessary.

REFERENCE NUMERALS

10: HEAT EXCHANGE REACTOR
20: ABSORPTION TANK
25: SEPARATION TANK
30: STRIPPER
40: ENDOTHERMIC REACTOR
50: EVAPORATION CONCENTRATOR
60: DEHYDRATING DISTILLATION TOWER
70: DISTILLATION TOWER
110, 120: MECHANICAL VAPOR RECOMPRESSOR

What is claimed is:

1. A system for energy recycling using mechanical vapor recompression in combined chemical process, characterized in that the system comprises:
    a heat exchange reactor (10) for generating an intermediate material by means of an exothermic reaction and discharging the generated intermediate material, and heat-exchanging heat generated in the exothermic reaction with water supplied from outside so as to generate water vapor;
    an absorption tank (20) for receiving the intermediate material, and mixing the intermediate material with water, so as to generate an intermediate material aqueous solution;
    a stripper (30) for receiving the intermediate material aqueous solution, and separating the intermediate material into an intermediate material gas and an intermediate material aqueous solution;
    an endothermic reactor (40) for receiving the intermediate material water-rich aqueous solution, and reacting the intermediate material with water, so as to produce a final product aqueous solution;
    an evaporation concentrator (50) for receiving the final product aqueous solution, and heat-exchanging heat of the water vapor from the heat exchange reactor with the final product aqueous solution so as to generate steam;
    a dehydrating distillation tower (60) for receiving, dehydrating, and purifying the final product aqueous solution discharged from the evaporation concentrator; and
    a mechanical vapor recompressor (110) for compressing the steam from the evaporation concentrator (50), and providing the compressed steam as a source of heat or a source of steam supply.

2. The system for energy recycling using mechanical vapor recompression in combined chemical process, according to claim 1,
    characterized in that the evaporation concentrator (50) is composed of a multi-stage evaporation concentrator in which a plurality of evaporation concentrators are sequentially connected, and the number of stages of the multi-stage evaporation concentrator is determined according to the temperature and pressure of the steam required in the mechanical vapor recompressor, in consideration of the concentration of the final product aqueous solution discharged from the evaporation concentrator and the amount of discharge heat of the water vapor generated in the heat exchange reactor.

3. The system for energy recycling using mechanical vapor recompression in combined chemical process, according to claim 2,
    characterized in that the evaporation concentrator forming the multi-stage evaporation concentrator is a natural circulation type evaporation concentrator.

4. The system for energy recycling using mechanical vapor recompression in combined chemical process, according to claim 2,
    characterized in that the evaporation concentrator forming the multi-stage evaporation concentrator is a falling film evaporator.

5. The system for energy recycling using mechanical vapor recompression in combined chemical process, according to claim 1,
    characterized in that the mechanical vapor recompressor (110) is in fluid communication with the endothermic reactor (40), such that the endothermic reactor (40) receives heat from the steam discharged from the mechanical vapor recompressor.

6. The system for energy recycling using mechanical vapor recompression in combined chemical process, according to claim 1,
    characterized in that a reboiler (69) of the dehydrating distillation tower (60) is in fluid communication with the mechanical vapor recompressor (110), such that the dehydrating distillation tower (60) receives heat from the steam.

7. The system for energy recycling using mechanical vapor recompression in combined chemical process, according to claim 1,
    characterized in that a reboiler (39) of the stripper (30) is in fluid communication with the mechanical vapor recompressor (110), such that the stripper (30) receives heat from the steam.

8. The system for energy recycling using mechanical vapor recompression in combined chemical process, according to claim 1,
    characterized in that the system further comprises a distillation tower (70) provided to condense the intermediate material gas discharged from the stripper (30) so as to receive the intermediate material as an intermediate material solution, and, in an upper portion of the distillation tower (70), to distill the intermediate material so as to discharge the intermediate material as a pure intermediate material, and, in a lower portion of the distillation tower (70), to discharge the remaining intermediate material solution so as to supply the remaining intermediate material solution to the endothermic reactor (40).

9. The system for energy recycling using mechanical vapor recompression in combined chemical process, according to claim 8,
characterized in that a reboiler (79) of the distillation tower (70) is in fluid communication with the mechanical vapor recompressor (110), such that the distillation tower (70) receives heat from the steam.

10. The system for energy recycling using mechanical vapor recompression in combined chemical process, according to claim 1,
characterized in that the steam of the mechanical vapor recompressor (110) is in fluid communication with a cooling water preheater of the heat exchange reactor so as to preheat cooling water supplied to the heat exchange reactor (10).

11. The system for energy recycling using mechanical vapor recompression in combined chemical process, according to claim 1,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

12. The system for energy recycling using mechanical vapor recompression in combined chemical process, according to claim 1,
characterized in that the intermediate material is ethylene oxide, and the final product is ethylene glycol.

13. The system for energy recycling using mechanical vapor recompression in combined chemical process, according to claim 2,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

14. The system for energy recycling using mechanical vapor recompression in combined chemical process, according to claim 3,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

15. The system for energy recycling using mechanical vapor recompression in combined chemical process, according to claim 4,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

16. The system for energy recycling using mechanical vapor recompression in combined chemical process, according to claim 5,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

17. The system for energy recycling using mechanical vapor recompression in combined chemical process, according to claim 6,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

18. The system for energy recycling using mechanical vapor recompression in combined chemical process, according to claim 7,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

19. The system for energy recycling using mechanical vapor recompression in combined chemical process, according to claim 8,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

20. The system for energy recycling using mechanical vapor recompression in combined chemical process, according to claim 9,
characterized in that a mechanical vapor recompressor (120) is additionally disposed between the mechanical vapor recompressor (110) and the stripper (30), or between the mechanical vapor recompressor (110) and the cooling water preheater of the heat exchange reactor (10).

* * * * *